United States Patent
Atac et al.

[11] Patent Number: 5,978,444
[45] Date of Patent: Nov. 2, 1999

[54] DIRECT DETECTION OF X-RAYS FOR PROTEIN CRYSTALLOGRAPHY EMPLOYING A THICK, LARGE AREA CCD

[75] Inventors: Muzaffer Atac, Wheaton, Ill.; Timothy McKay, Ann Arbor, Mich.

[73] Assignee: The United States of America as represented by the United States Department of Energy, Washington, D.C.

[21] Appl. No.: 09/000,880

[22] Filed: Dec. 30, 1997

[51] Int. Cl.$^6$ .............................. G01N 23/20; H05G 1/64
[52] U.S. Cl. .............................. 378/73; 378/98.8
[58] Field of Search .................. 378/73, 82, 86, 378/58.8; 250/370.09

[56] References Cited

U.S. PATENT DOCUMENTS

| | | | |
|---|---|---|---|
| 5,077,767 | 12/1991 | Gaukroger | 378/73 |
| 5,193,104 | 3/1993 | Bastie et al. | 378/73 |
| 5,262,649 | 11/1993 | Antonuk et al. | 250/370.09 |
| 5,636,258 | 6/1997 | Okumura et al. | 378/73 |
| 5,742,659 | 4/1998 | Atac et al. | 378/98.8 |
| 5,864,599 | 1/1999 | Cowan et al. | 378/73 |
| 5,912,942 | 6/1999 | Schick et al. | 378/98.8 |

FOREIGN PATENT DOCUMENTS

94/15202   7/1994   Germany ................................. 378/73

*Primary Examiner*—David P. Porta
*Assistant Examiner*—Drew A. Dunn
*Attorney, Agent, or Firm*—Bradley W. Smith; Mark P. Dvorscak; William R. Moser

[57] ABSTRACT

An apparatus and method for directly determining the crystalline structure of a protein crystal. The crystal is irradiated by a finely collimated x-ray beam. The interaction of the x-ray beam with the crystal produces scattered x-rays. These scattered x-rays are detected by means of a large area, thick CCD which is capable of measuring a significant number of scattered x-rays which impact its surface. The CCD is capable of detecting the position of impact of the scattered x-ray on the surface of the CCD and the quantity of scattered x-rays which impact the same cell or pixel. This data is then processed in real-time and the processed data is outputted to produce a image of the structure of the crystal. If this crystal is a protein the molecular structure of the protein can be determined from the data received.

14 Claims, 4 Drawing Sheets

DIRECT DETECTION OF X-RAYS FOR PROTEIN CRYSTALLOGRAPHY EMPLOYING A THICK, LARGE AREA CCD

CONTRACTUAL ORIGIN OF THE INVENTION

The United States Government has rights in this invention pursuant to Contract No. DE-AC02-76CH03000 between the U.S. Department of Energy and the University Research Association.

BACKGROUND OF THE INVENTION

This invention relates to the use of a charged coupled device (CCD) for the direct detection of scattered x-rays used in the determination of the structure of a protein crystal.

Currently, the scattered x-rays used to determine the structure of a crystalline material are detected using film or in the alternative a scintillating or phosphorescent material which when illuminated by a scattered x-ray gives off a visible light. In the latter case the phosphor is coupled with a device which is capable of detecting the light given off by the phosphor and converting it into electronic data which is used to determine the position and intensity of the scattered x-rays. Often a CCD is used in conjunction with the phosphor to determine the position and frequency of the x-rays which are scattered off of a crystallized version of a molecule. With a CCD a single photon can generate a measurable electrical charge. The CCD employs a two dimensional array of cells or pixels, each of which acts as an independent x-ray detector, thus, allowing many scattered x-rays to be stored in the cells of the CCD and then read and recorded.

Generally, CCD-based imaging devices compromise sensitivity and resolution due to smearing and spatial distortion of the image caused by the presence of the scintillating or phosphorescent material between the crystal and the CCD. This is due to the alteration of the path of the x-rays upon interacting with the scintillating or phosphor material. Since, after the x-ray interacts with the light emitting material, the photons emitted do not necessarily follow the exact path of the initial x-ray. This results in a decrease in the resolution or a smearing of the measured point of impact on the CCD of two successive x-rays traveling along the same or close to the same path.

As related above, the prior art CCD-based imagery employs an intermediate light generating transducer, such as a phosphor, to transform the incident x-rays to a light source. The photons from the light source are converted by the CCD to electrical signals. The conversion step of using the phosphor was instituted with the x-rays since the majority of x-rays striking a typical CCD would pass through the CCD without detection. This results from the CCD being too thin.

An alternate method of detection was proposed by Antonuk et al. as described in U.S. Pat. No. 5,262,649, in which, the use of a CCD is avoided in lieu of a thin film amorphous silicon device. Antonuk's patent teaches a thin-film, flat panel, pixelated detector array which serves as a real-time digital image and dosimeter for x-rays or gamma rays. The detector is a plurality of photodiodes made of hydrogenated amorphous silicon arrayed in columns and rows on a glass substrate. Each photodiode is connected to a thin film field effect transistor also located on the glass substrate; the combination of which forms one pixel. For megavoltage beams, a photon to electron conversion layer is located directly above and in contact with a phosphor or scintillating layer. Since each sensor is adjacent to and connected to its corresponding field effect transistor, the area available for detection in reference to the total area of the detector is drastically reduced.

Applicants in their invention provide for the direct detection of the scattered x-rays without an intermediate phosphor or scintillation layer. By using a large area, thick CCD device, applicants can detect the scattered x-rays directly and on a real-time basis. Use of a thick CCD as a direct detection device for use in detecting breast cancer is described in U.S. patent application entitled "High Resolution Mammography", Ser. No. 08/697,536, filing date Aug. 26, 1996, now U.S. Pat. No. 5,742,659, which is incorporated herein in its entirety by reference.

One object of this invention is provide a device which is capable of directly discerning, in real-time, the frequency and position of x-rays scattered by a protein crystal initially subjected to an incident x-ray beam.

Another object of this invention is the employment of a large area, thick CCD to provide a high resolution image of the pattern generated by the scattered x-rays resulting from the interaction of the protein crystal and the incident x-ray beam.

Additional advantages, objects and novel features of the invention will become apparent to those skilled in the art upon examination of the following and by practice of the invention.

SUMMARY OF THE INVENTION

To achieve the foregoing and other advantages, this invention comprises an apparatus for real-time, direct detection of x-rays impacting on the surface of a large area, thick charge coupled device (CCD). The CCD is positioned to detect the scattered x-rays resulting from the interaction of an initial incident x-ray beam and a protein crystal. By employing CCD technology, the frequency and position of the scattered x-rays can be detected on a real-time basis and with high resolution.

The CCD is functionally divided into storage cells or pixels, each of which stores an electrical count which indicative of the number of x-rays detected by the cell. A pattern generator receives the electrical signal from the CCD in the form of a stored count. The display device then displays the image representation of the count data which has been processed by the image processing system.

BRIEF DESCRIPTION OF THE DRAWINGS

The present invention is illustrated in the accompanying drawing where.

DETAILED DESCRIPTION OF THE INVENTION

Figure 1:
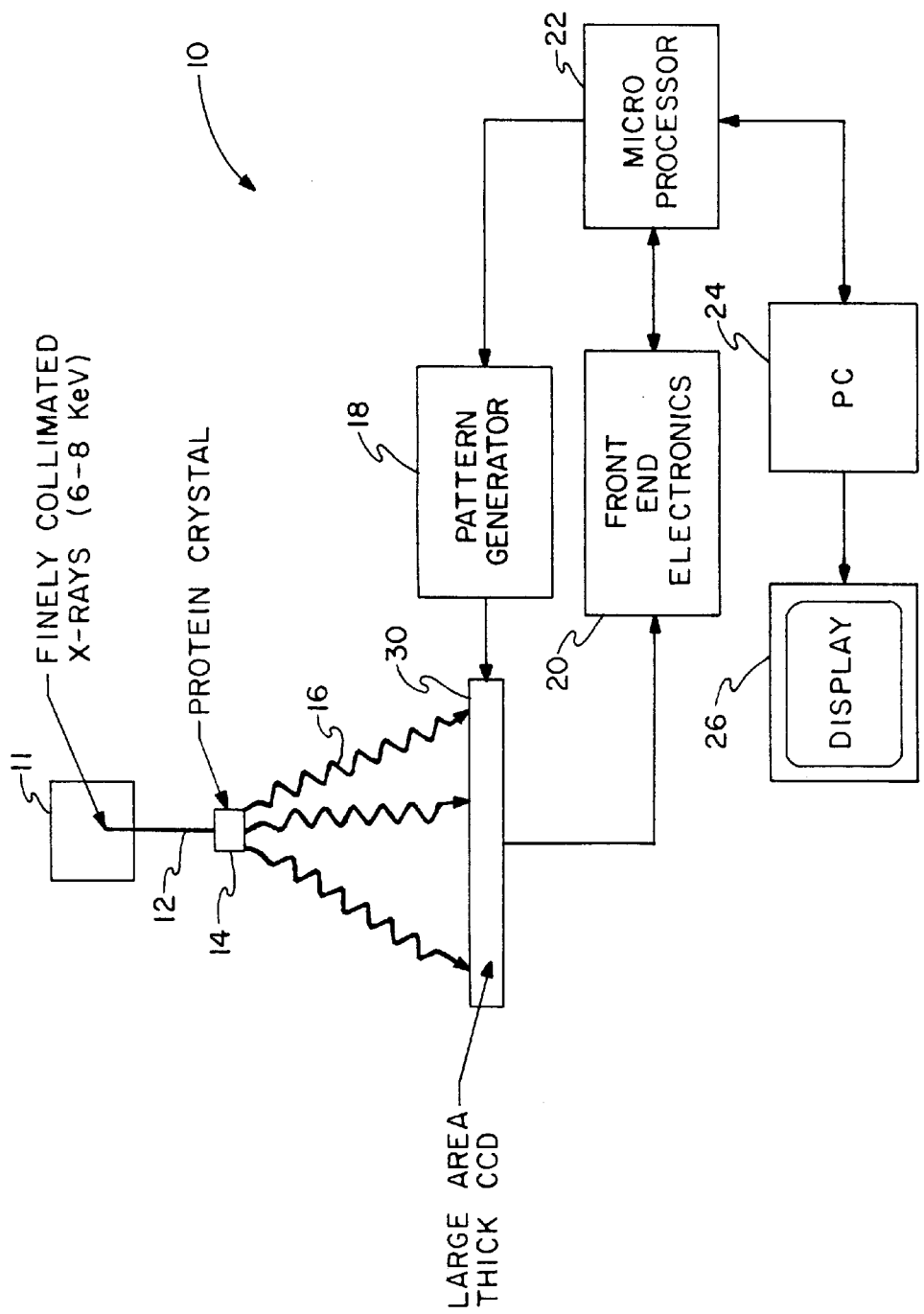
FIG. 1 is a schematic of a protein x-ray crystallography apparatus using a high resolution CCD.

FIG. 1 depicts the x-ray crystallography apparatus, 10, for the determination of the structure of protein crystals. A x-ray source, 11, is used to generate a finely collimated beam of x-rays, 12, which irradiates a protein crystal, 14. By measuring the position and intensity of the scattered x-rays, 16, resulting from the interaction of the protein crystal and the collimated incident x-ray beam, 12, the structure of the protein crystal, 14, is determined. The scattered x-rays, 16, are detected by a thick, large area CCD, 30, located at a known position relative to the position and orientation of the protein crystal, 14, and the incident x-ray beam, 12. The pattern generator, 18, is electrically coupled to the CCD, 30. The pattern generator, 18, controls the output of the cells making up the CCD. The stored count of each cell of the CCD can be outputted individually or, in the alternative, the counts from multiple cells can be combined prior to output. This practice is referred to as "binning". By employing varying degrees of binning of the cells, the resolution of the output can be controlled. The front end electronics, 20, control the operation of the apparatus through the microprocessor, 22. The microprocessor, 22, is coupled to programmed computer, 24, and display, 26, which provides a visual display of the data detected by the CCD, 30 and with a resulting hard copy. The computer, 24, is capable of directing the storage of the data on disk or tape.

Figure 2:
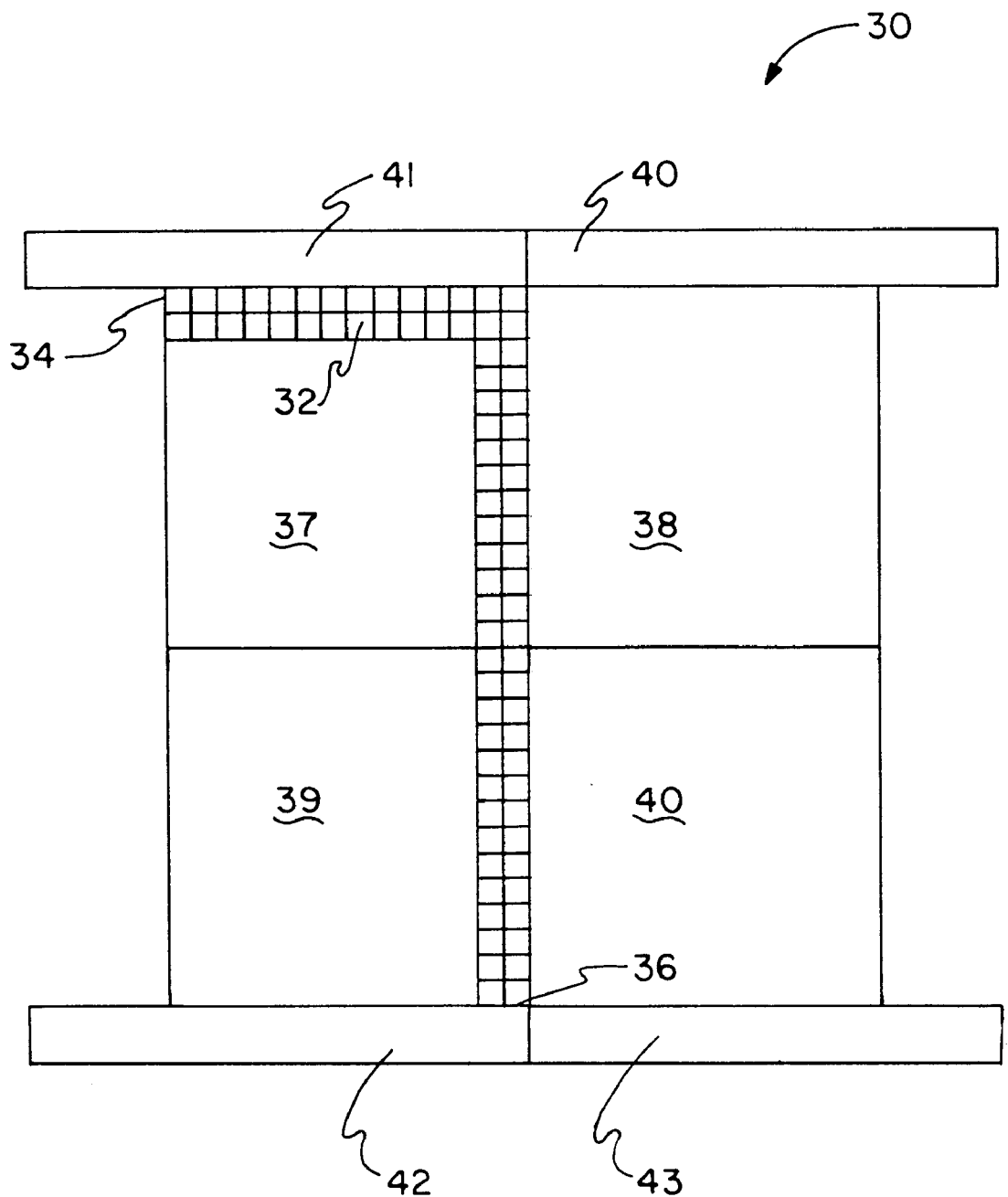
FIG. 2 is a top view of a charge coupled device as utilized in the subject invention.

FIG. 2 depicts a top plan view of the charge coupled device (CCD), 30. The CCD, 30, is divided into a matrix of individual cells, 32, arranged in a series of rows, 34, and columns, 36. Each cell, 32, temporarily stores an electrical signal or count which is representative of the number of scattered x-rays incident on and detected by the CCD cell. Upon completion of the irradiation process, the data is downloaded and used to produce an image of the structure of the irradiated protein crystal.

An alternate configuration can be established by partitioning the CCD. For example, the CCD can be partitioned into quadrants, 37–40. The output registers can be arranged in such a manner that each group of cells comprising the quadrant can output through a specific register, 40–43, so that, for example, the data from quadrant 37 outputs through output register 41.

Figure 3:
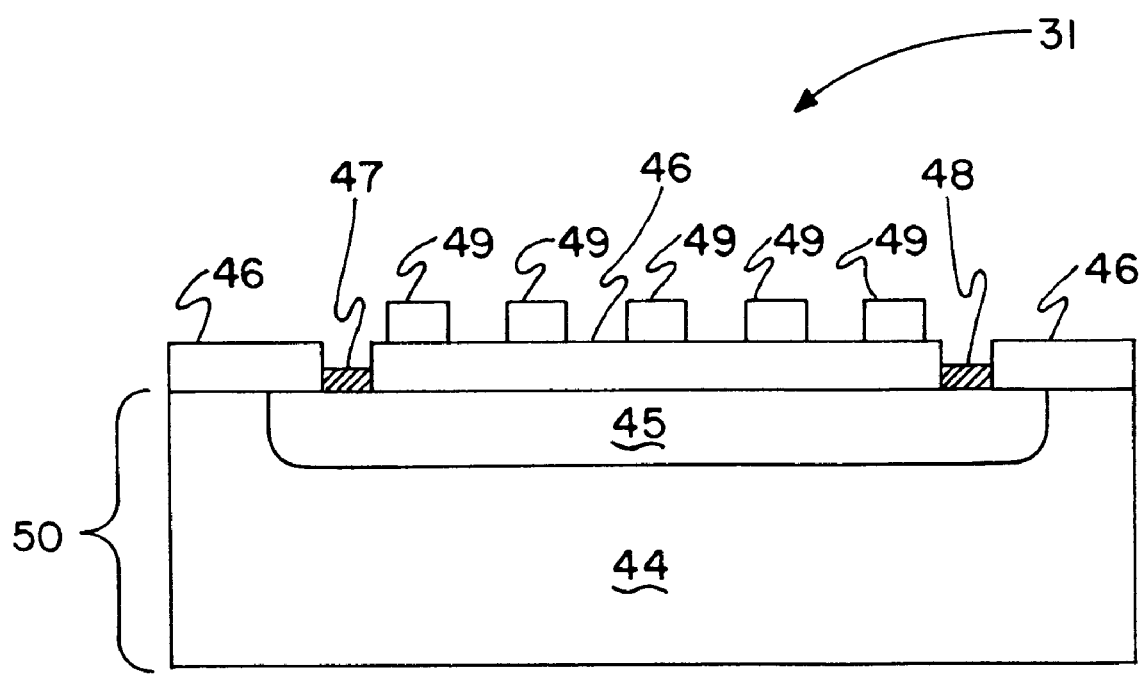
FIG. 3 is a cross-section of part of the internal structure of a buried channel CCD.

In FIG. 3, for the subject embodiment, a buried channel charge coupled device is employed, 31. In the present case, a p-type substrate, 44, is utilized with an n-type buried channel, 45. A silicon oxide layer, 46, resides on top of the p-type substrate. Output electrodes, 47 and 48, are located in the gaps in the silicon oxide layer, 46. Transfer electrodes, 49, rest on the silicon oxide layer, 46. Selective electrical potentials are applied to electrodes, 49, to define the cells, 32. Applying a bias to transfer electrodes, 49, causes stored electrical counts to shift between cells to the output electrodes 47 and 48. The transfer electrodes, 49, employed to form the cells or pixels of the CCD allow the passage of x-rays, thus, making the entire upper surface of the CCD receptive to x-rays. As x-rays interact with each cell, 32, of the CCD, the energy of the x-ray is absorbed to provide an electron hole pair within the cell. Thus, the number of electron hole pairs within a cell is proportional to the number of incident, detected x-rays. When this information is transferred to the imaging system, the light intensity of the image, of the imaging system, corresponds to the count in a corresponding cell.

However, not all of the x-rays incident on the surface of the CCD are detected and converted into electrons. The conversion efficiency of the CCD is proportional to its thickness, 50, FIG. 3, of the CCD, 31. The conversion efficiency increases as the CCD thickness increases. Preferably the thickness of the CCD varies between 30 and 500 microns. An optimum range would be between 60 and 300 microns. The conversion efficiency is 65% for a CCD having a thickness of 60 microns. A typical CCD may include a matrix of cells, 32, 2,048 by 2,048 where each cell has surface measurements of 24×24 microns.

The CCD employed with the subject invention has a large dynamic range allowing it to detect and count a large number of incident x-rays. This results from the cells being capable of storing a large number of electron holes without becoming saturated. The large dynamic range enhances the contrast experienced between cells during the detection process.

Figure 4:
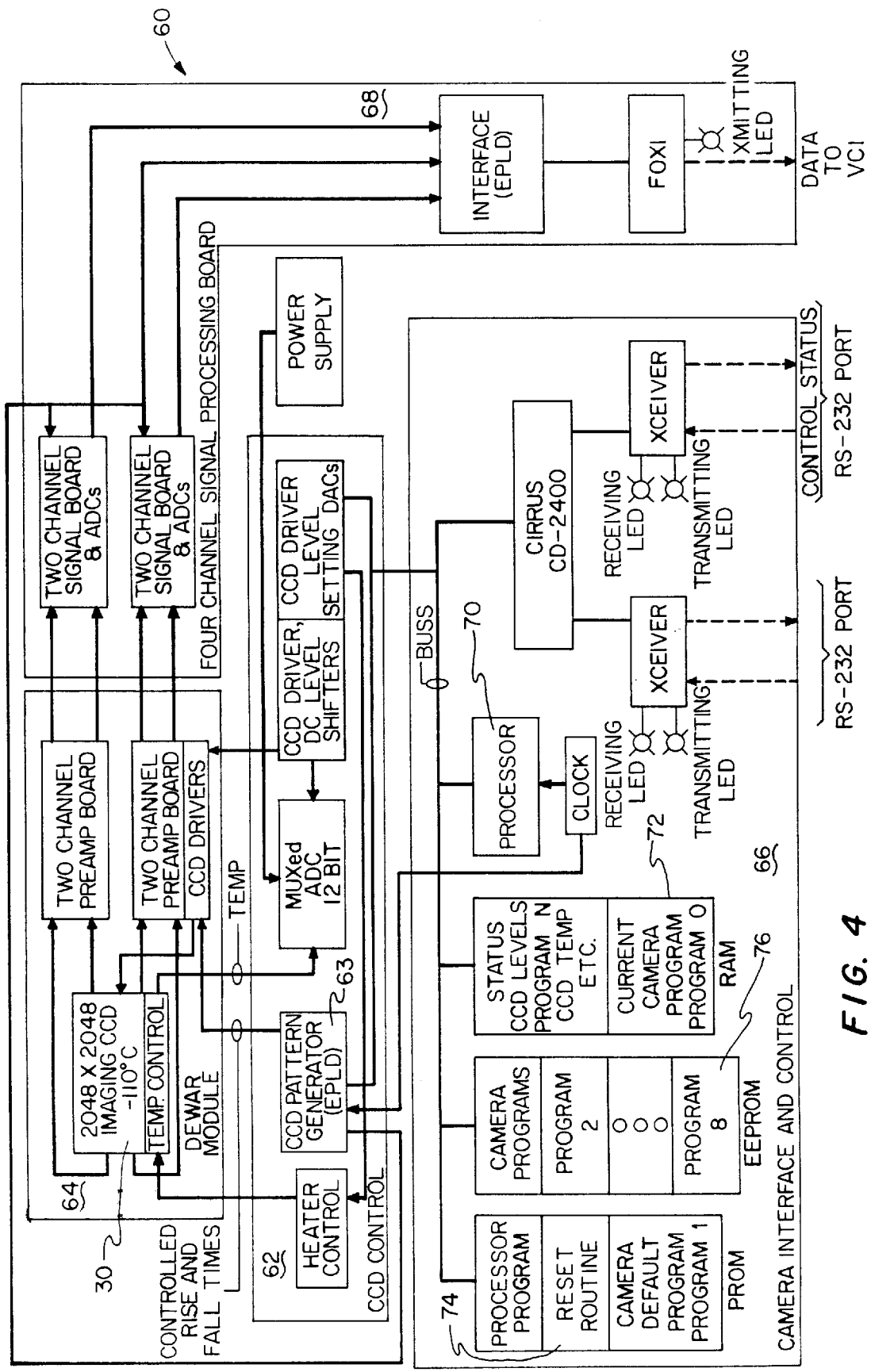
FIG. 4 is a schematic depicting the front end electronics of the x-ray crystallography apparatus.

The CCD processor 60, FIG. 4, comprising items 18, 20, and 22 of FIG. 1 is shown in more detail in FIG. 4. FIG. 4 includes a CCD controller, 62, a dewar module 64, a camera interface, 66, and a multi-channel signal processing board, 68. The CCD controller, 62, sets the CCD timing patterns and the voltage levels. It, also, controls the CCD operating temperature and monitors the voltage levels of the camera electronics. To control thermal electron noise, the CCD operates at a temperature of approximately −110 degree C. Although, this temperature is allowed to vary somewhat in response to the optimal thermal electron current. The subject temperature control apparatus found in the CCD control, 62, controls the temperature to within one degree C. The camera interface, 66, includes processor, 70, which remotely controls the CCD controller, 62. The camera interface, 66, also, includes RAM, 72, which provides memory for the system, and PROM, 74, stores the processor program, the reset routine and the camera default program. The EEPROM, 76, contains the camera programs.

The CCD controller, 62, includes a line shifter, a pattern generator, 63, and a level setting digital to analog converter. The pattern generator, 63, is in communication with the DEWAR module, 64. The DEWAR module, 62, includes the CCD, 30, a CCD driver and a pair of two channel amplifiers. The CCD driver is electrically connected to the transfer electrodes, 49, of the CCD and functions to create cells within the CCD and to shift counts within the CCD in response to a signal received from the pattern generator, 63.

On the application of power, the processor, 70, loads a set of operating parameters from the PROM into the RAM. The pattern generator, 63, generates a pattern of signals for the CCD driver to control the CCD. The pattern generator is set to a subsection mode when only a subsection of the pixels or cells of the CCD are to be read out.

In the alternative, materials other than silicon can be used to form the CCD. These materials include Gallium Arsenide (GaAs), Gallium Nitride (GaN) and the like. Since these materials are denser than silicon, the conversion efficiency of the CCD with respect to x-rays is increased.

The subject invention provides a high resolution, real-time readout of the position and intensity of the scattered x-rays produced when a crystal is irradiated by an incident beam. By changing the position of the CCD or by providing encircling three dimensional coverage, the position and intensity of scattered x-ray can be determined. This information allows one to quickly determine the structure of the crystal or in the case of a protein crystal, the structure of the protein. The data can be viewed directly on a monitor or stored for further compilation. The thick CCD is sized so that the efficiency of detection is between 65%–70%.

This invention is not limited to the determination of the structure of a protein crystal. The structure associated with the interaction of an organic molecule with the protein can be determined from its crystallized structure by implementation of this apparatus. Also, the structure of other biological molecules with or without the interaction of an organic molecule can be determined.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The embodiment of this invention in which an exclusive property or privilege is claimed is defined as follows:

1. A high resolution imaging system for determining a structure for a crystal by direct detection of x-rays scattered by the crystal in response to an incident x-ray beam comprising:

an energy source for producing a finely collimated beam of x-rays directed towards a crystal the structure of which is to be determined;

a crystal positioned so as to intercept and scatter said x-ray beam thereby producing a pattern of scattered x-rays which is representative of the structure of the crystal;

a thick, large area charged coupled device positioned to directly intercept and detect said scattered x-rays where said charged coupled device is divided into a matrix of cells each of which is capable of detecting and storing counts representative of said scattered x-rays incident on the charged coupled device;

a CCD controller electrically coupled to said charge coupled device where said controller controls the acquisition of data from said charged coupled device;

a signal processing system coupled to said CCD for processing the data from the CCD;

a display system coupled to said signal processing system where said display system displays processed data visually or records it digitally;

a camera control system coupled to said CCD controller where said control system exercises control over said CCD controller.

2. The imaging system of claim 1 wherein said charge coupled device has a thickness of at least 60 microns.

3. The imaging system of claim 1 wherein the said charge coupled device has a thickness of at least 250 microns.

4. The imaging system of claim 1 wherein said charge coupled device includes a matrix of at least 2048×2048 cells or pixels where each cell or pixel is sized at approximately 24×24 microns.

5. The imaging system of claim 1 wherein said charged coupled device has an energy efficiency of approximately 65% for detecting x-rays having an energy of approximately 6 KeV.

6. The imaging system of claim 1 wherein said CCD controller includes a means for controlling the temperature of the CCD to control the thermal electron noise charge.

7. The imaging system of claim 1 wherein said crystal is a protein crystal.

8. The imaging system of claim 1 wherein said crystal is a protein coupled with an organic molecule.

9. The imaging system of claim 1 wherein the energy of the finely collimated x-ray beam is between 6 to 8 KeV.

10. A method for determining the crystalline structure of a crystal by direct measurement of scattered x-rays including:

positioning an x-ray source at a specified location with respect to the crystal;

irradiating the crystal with a finely collimated x-ray beam;

orientating a thick, large area CCD at a specified location with respect to the crystal;

detecting a plurality scattered x-rays by means of said CCD where said scattered x-rays result from the interaction of said collimated x-ray beam and the crystal;

determining a position and intensity of the scattered x-rays striking said CCD;

repositioning said CCD to plot said plurality of scattered xrays originating from the crystal;

determining the crystalline structure of said crystal based on the position and intensity of said scattered x-rays detected by said CCD.

11. The method of claim 10 including selecting as said crystal a protein crystal.

12. The method of claim 10 including selecting as said crystal a crystal encompassing an organic molecule coupled to a protein.

13. The method of claim 10 including sizing said thick CCD so as to directly detect a significant portion of said scattered x-rays striking said CCD.

14. The method of claim 10 including measuring the position and intensity of said scattered x-rays incident on said CCD in real time.

* * * * *